United States Patent
Dorn

(10) Patent No.: US 11,568,969 B2
(45) Date of Patent: Jan. 31, 2023

(54) EVALUATING DOSE EVENTS OF MEDICAL IMAGING EXAMS

(71) Applicant: Siemens Healthcare GmbH, Erlangen (DE)

(72) Inventor: Karlheinz Dorn, Kalchreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 649 days.

(21) Appl. No.: 16/554,997

(22) Filed: Aug. 29, 2019

(65) Prior Publication Data

US 2020/0069277 A1    Mar. 5, 2020

(30) Foreign Application Priority Data

Aug. 31, 2018 (EP) .................................. 8192023

(51) Int. Cl.
*G16H 50/30*    (2018.01)
*G16H 10/60*    (2018.01)
(Continued)

(52) U.S. Cl.
CPC ............ *G16H 10/60* (2018.01); *G16H 20/40* (2018.01); *G16H 30/20* (2018.01); *G16H 50/30* (2018.01)

(58) Field of Classification Search
None
See application file for complete search history.

(56) References Cited

U.S. PATENT DOCUMENTS

| 10,289,953 | B2 * | 5/2019 | Lee ..................... | A61B 6/032 |
| 2005/0209888 | A1 * | 9/2005 | Oowaki ................. | G06Q 10/10 |
| | | | | 705/3 |

(Continued)

FOREIGN PATENT DOCUMENTS

| WO | WO 2007062178 A2 | 5/2007 |
| WO | WO 2011137374 A1 | 11/2011 |

OTHER PUBLICATIONS

Colang, J. E., Killion, J. B., & Vano, E. (2007). Patient dose from CT: A literature review. Radiologic Technology, 79(1), 17(10). Retrieved from https://dialog.proquest.com/professional/docview/769105132?accountid=131444 (Year: 2007).*
European Office Action dated Feb. 4, 2021.
"RadLex Playbook 2.5 User Guide"; by RSNA Informatics; Version 2.5; Feb. 2018; from http://playbook.radlex.org/playbaok/SearchRadlexAction.

(Continued)

*Primary Examiner* — Robert A Sorey

(74) *Attorney, Agent, or Firm* — Harness, Dickey & Pierce, P.L.C.

(57) ABSTRACT

A computer-implemented method, as well as a system, is for evaluating dose events of at least one medical imaging exam. In an embodiment, the method includes receiving at least one list of dose events of the at least one medical imaging exam; providing a body region counter value indicating a number of body regions; determining whether the body region counter value is 1 or larger than 1; associating, upon the body region counter value provided being 1, all of the dose events with a standardized body region based protocol identifier; and associating, upon the value being larger than 1, each dose event with at least one standardized body region based protocol identifier, each of the dose events being respectively associated with a number of different standardized body region based protocol identifiers, with which each of the dose events are associated, is equal to the body region counter value provided.

23 Claims, 3 Drawing Sheets

(51) Int. Cl.
   *G16H 20/40* (2018.01)
   *G16H 30/20* (2018.01)

(56) References Cited

U.S. PATENT DOCUMENTS

| | | | | |
|---|---|---|---|---|
| 2008/0103834 A1* | 5/2008 | Reiner | G16H 20/40 | 705/3 |
| 2008/0292065 A1 | 11/2008 | Bppme | | |
| 2010/0042434 A1* | 2/2010 | Luo | G16H 50/20 | 705/3 |
| 2012/0106817 A1 | 5/2012 | Shih et al. | | |
| 2013/0279644 A1* | 10/2013 | Yanagida | A61B 6/10 | 378/8 |
| 2015/0100290 A1* | 4/2015 | Falt | G16H 50/50 | 703/2 |
| 2017/0124290 A1* | 5/2017 | Hegde | G16H 30/20 | |

OTHER PUBLICATIONS

"Exam Name Mapping Tool"; User Guide; by NRDR—National Radiology Data Registry Support; Aug. 23, 2018; https://nrdrsupport.acr.org/support/solutions/articles/11009041532-exam-name-mapping-tool.

Digital Imaging and Communications in Medicine (DICOM); Part 1: "Introduction and Overview"; Version PS3.1 2018c; 2018; from https://www.dicomstandard.org/current/.

"RadLex Playbook and the LOINC/RSNA Radiology Playbook"; by RSNA; https://www.rsna.org/RadLex_Playbook.aspx; Sep. 18, 2018.

McDonald, Clem et at:"LOINC Users' Guide"; by Regenstrief Institute; Version 2.64; Jun. 2018; from www.loinc.org.

European Extended Search Report for Application No. 18192023.2 dated Mar. 6, 2019.

* cited by examiner

EVALUATING DOSE EVENTS OF MEDICAL IMAGING EXAMS

PRIORITY STATEMENT

The present application hereby claims priority under 35 U.S.C. § 119 to European patent application number EP18192023.2 filed Aug. 31, 2018, the entire contents of which are hereby incorporated herein by reference.

FIELD

At least one embodiment of the invention generally relates to data analysis of complete medical exams as well as of individual groups of scans to support both 1:1 or n:m mapping to protocols based on standardized ontologies.

At least one embodiment of the invention further generally relates to methods and systems of evaluating dose events of medical imaging exams, in particular with the intention of comparing them to reference values when they have been mapped to a standardized set of protocols. The mapping may be performed in a 1:1 ratio of exams to protocols, or in an n:m ratio, wherein n and m are different integers.

BACKGROUND

Nowadays, a large number of non-invasive medical imaging techniques is available to better investigate and diagnose the medical status of a patient.

Most non-invasive medical imaging techniques subject the patient to a dose of electromagnetic radiation in individual scans, which can therefore be designated as "dose events". Accordingly, there is a demand to keep track of such dose events in order to maintain awareness of the total amount of electromagnetic radiation applied to a patient over time. Dose amounts can be accumulated and compared to reference values to determine whether additional dose amounts may be applied or not.

Medical imaging modalities such as computer tomography (CT) scanners, mammography scanners, Molecular-Imaging scanners, x-ray devices and so on usually provide lists of individual dose events (or: scans) that have been performed. However, an increasing level of detail in most medical imaging techniques and an increasingly large number of precise anatomic locations that can be examined (or: scanned) lead to a sometimes confusing multitude of dose event lists and codes.

Ontologies such as the RadLex ontology have been introduced in order to standardize data recording formats such that dose events can be noted and archived even if they stem from different modalities at different tenants using different scanning equipment.

For example, the "RadLex Playbook" (registered trademark) introduced by the Radiological Society of North America (RSNA) constitutes a portion of the RadLex ontology (meanwhile also part of the more general LOINC standard). The RadLex Playbook aims to provide a standard system for naming radiology procedures, based on the elements which define an imaging exam such as modality and body part, among others. By providing standard names and codes for radiologic studies, the RadLex Playbook is intended to facilitate a variety of operational and quality improvement efforts, including radiation dose tracking and image exchange.

Whenever mention is made herein of the RadLex (registered trademark) ontology, it is referred to the current RadLex version 2.5 released in February 2018. However, the concepts described herein may be equally applicable for future version of the standard. More information about the RadLex Playbook can e.g. be obtained from https://www.rsna.org/RadLex_Playbook.aspx.

Other projects include, e.g., the LOINC-RSNA Radiology Playbook which is jointly managed by the Regenstrief Institute (publisher of LOINC) and RSNA. This harmonized Playbook defines a new information model for describing imaging procedures, and identifies correspondences between RadLex Playbook codes and LOINC codes.

Whenever mention is made herein of LOINC (registered trademark) herein, it is referred to the LOINC version 2.64 released on Jun. 15, 2018, as is available e.g. from https://loinc.org/. However, the concepts described herein may be equally applicable for future version of the standard.

When dose events are applied, i.e. when electromagnetic radiation is applied to a patient, often merely a small body part ("anatomic focus") is of interest.

An anatomic focus may e.g. be, or comprise, an internal organ, a bone, a blood vessel, a gland, a muscle, a sinew and/or a limb.

For example, the anatomic focus may comprise, or consist of, an abdomen wall, an acetabulum, an acromioclavicular joint, additional gestation, an adrenal gland, an airway, an ankle, an aorta, an aortic root, an appendix, an aqueduct, an arm, an arterial anastomosis, an artery or multiple arteries, arteriovenous fistulae, an axilla, an axillary lymph node, biliary ducts, a biliary system, a bladder, bone marrow, a brachial artery, a brachial plexus, a brachiocephalic artery, a brain, a brainstem, a calcaneus, a calf, a carotid artery, a carpal bone, a carpal canal, a carpal tunnel, a celiac plexus, cerebral arteries, cerebral cisterns, cerebral sinuses, cervical arteries, a cervix, a chest wall, cholangiopancreatic ducts, cholecystokinin, a circle of willis, a clavicle, a coccys, coronary arteries, coronary veins, a cortex, a cyst, a deep cervical lymph node, a diaphragm, a DMSA, a duodenum, a dural venous sinus, an ear, an elbow, an endoleak, an endoscopy, an epidural space, an esophagography, an esophagus, an external auditory canal, a facet joint, facial bones, a fallopian tube, a femoral artery, a femur, a fetus, a fibula, a digit, a finger, a foot, a forearm, a gallbladder, a ganglion cyst, a gastrointestinal tract, genitals, a groin, a groin lymph node, a guide wire placement, a hallux, a hand, a heart, a hepatic vein, HIP, a humerus, an ileal conduit, an iliac artery, iliac vessels, an inferior vena cava, intercostal arteries, intercostal nerves, an intermediate joint, an internal auditory canal, an internal mammary artery, an intervertebral disc, an intra-articular contrast, a jaw, a joint, a jugular vein, a kidney, kidney vessels, a knee, a large intestine, a larynx, a left atrium, a ligament, a liver and/or the like.

However, due to the nature of electromagnetic radiation, a whole body region (e.g. the entire head, or the entire abdomen) might be affected by the same scan. When a medical imaging exam comprises a number of individual dose events, it is generally tried to determine a body region to which the dose events, or a majority of dose events, have been applied, and to associate the individual dose events with said determined body region. The exam is often performed with the help of a local exam protocol which is not standardized and different among scanner manufacturers, modalities and institutions which are using the scanner devices. In order to be able to compare exams and protocols among manufacturers and institutions the local protocols used are advantageously mapped to a standardized set of protocols. This is sometimes called an association with a standard protocol.

For example, all scans of an exam may be associated with a single body region (e.g. hand or abdomen or pelvis or neck or extremities et cetera) and the results may be stored in a single "study" according to the DICOM standard.

DICOM (registered trademark) refers to "Digital Imaging and Communications in Medicine" and is an international standard to transmit, store, retrieve, print, process and display medical imaging information. Whenever mention is made of DICOM herein, it is referred to the DICOM version DICOM PS3.1 2018c. However, the concepts described herein may be equally applicable for future version of the standard.

However, especially when medical imaging exams consist of a long list of individual dose events, it is potentially challenging to correctly associate all of the individual dose events with a single body region.

Such associating of dose events with body regions is important, however: national agencies as well as institutions have defined dose reference values for body regions with the intention that the accumulated dose values of the combined individual scans of the exam shall not, or at least not with good cause, exceed the reference values.

If, for a planned dose event, dose values are predicted for that would exceed the corresponding reference values, typically a dose alert is often created in order to strengthen awareness dose management to protect patients from too high dose values. Such a dose alert may prevent a medical technician or physician from performing an additional medical imaging scan.

Dose management products supporting benchmarking functionality usually need to map local exam protocols to a standard or ontology as described in the foregoing. Based on standardised body region based protocol identifiers (e.g. RPID 315 of the RadLex Playbook) a comparison between different exams (e.g. head exams) from different tenants with different scanner devices from different manufacturers can be accomplished when the individual exam has been mapped to the standard protocol before the comparison is to start. The mapping between exam and protocol is typically 1:1.

Additionally, situations may arise where a specific dose reference value is given for a certain exam but does not take into account that said exam is performed over a plurality of separate body regions. In that case, a dose alert may be automatically provided by a system because a total dose value is estimated to be too high even though actually the dose values applied to the different body regions would, each by themselves, be well below the provided reference value for those individual body regions separately.

An example mapping (or: associating) is performed e.g. by the "Exam Name Mapping Tool" of the US-American Dose Index Registry (DIR), see also the US-American National Radiology Data Registry Support (NRDR).

SUMMARY

The inventors have discovered that the aforementioned 1:1 mapping can, however, lead to situations where a complete exam cannot be mapped to a standards-based protocol because a specific standard might not have a protocol with the relevant body regions available. The inventors have discovered that this is especially true when the institutions are performing a single exam consisting of multiple scans (each scan being equivalent to a single dose event) crossing multiple different body regions because standards do not provide standard protocols for all possible permutations.

Moreover, the inventors have discovered that when dose events from, for example, different studies are compiled to determine a total of dose events for a specific patient (accumulating dose values), it is sometimes possible that multiple instances (or: duplicates) of the same real-world dose event are present in the compilation and that therefore an exaggerated picture of the dose amount of the dose events for that specific patient is created.

The inventors have discovered that this case may occur when a study, which may comprise several series, each series e.g. comprising lists of dose events, images and/or reports, is partially copied. For example, a study may comprise images of a head and images of a chest of a patient. A tenant may copy the study, remove the images of the chest from one instance of the study and send the remaining study to a radiologist specialized in heads. In the other instance, the tenant may remove the images of the head and send the remaining study to a radiologist specialized in chests. However, in both of these studies the same list or lists of dose events (e.g. dose reports) are kept. When the two instances of the study are then re-compiled, the list (or lists) of dose events is/are duplicated. The inventors have discovered that this may create the impression that twice the actual dose amount has been applied to the patient.

At least one embodiment of the present invention therefore provides an improved method for evaluating dose events, as well as providing an improved system for evaluating dose events.

In the following, solutions according to embodiments of the invention are described with respect to different aspects comprising claimed systems as well as claimed methods. Features, advantages or alternative embodiments herein can be assigned to the other claimed aspects and/or objects and vice versa. In other words, claims for the system and other aspects of the invention can be improved with features described or claimed in the context of the method, and vice versa. In this case, the functional features of the method are embodied by objective units of the system.

Accordingly, according to a first embodiment of the present invention, a computer-implemented method for evaluating dose events of at least one medical imaging exam is provided, comprising:

receiving at least one list of dose events of the at least one medical imaging exam;

providing a body region counter value indicating a number of body regions;

determining whether the body region counter value is 1 or larger than 1;

associating, when the provided body region counter value is 1, all of the dose events of the at least one list with a standardized body region based protocol identifier;

associating, when the provided body region counter value is larger than 1, each dose event of the at least one list with at least one standardized body region based protocol identifier in such a way that the dose events are associated with a number of different standardized body region based protocol identifiers, wherein the number of different standardized body region based protocol identifiers with which dose events are associated is equal to the provided body region counter value.

According to a second embodiment of the present invention, a system for evaluating dose events of at least one medical imaging exam is provided, comprising:

at least one processor configured to implement:

an input module to receive at least one list of dose events of the at least one medical imaging exam;

a region counter module to provide a body region counter value indicating a number of body regions;

a counting module to determine whether the body region counter value is 1 or larger than 1; and an associating module to associate, upon the body region counter value provided being 1, all of the dose events of the at least one list of dose events, with a standardized body region based protocol identifier; the at least one processor being further configured to associate, upon the body region counter value provided being larger than 1, each dose event of the at least one list of dose events, with at least one standardized body region based protocol identifier, each of the dose events being respectively associated with a number of different standardized body region based protocol identifiers, wherein the number of different standardized body region based protocol identifiers, with which each of the dose events are associated, is equal to the body region counter value provided.

According to a third embodiment of the present invention, a non-transitory computer-readable storage medium is provided that stores executable program code configured to, when executed by at least one processor (in particular when executed by the system according to the second embodiment of the invention), perform the method according to the first embodiment.

According to a possible fourth embodiment of the present invention, a computer program product is provided that comprises executable program code configured to, when executed (in particular when executed by the system according to the second embodiment of the invention), perform the method according to the first embodiment.

According to a possible fifth embodiment of the present invention, a data stream is provided that comprises, or is configured to generate, executable program code configured to, when executed (in particular when executed by the system according to the second embodiment of the invention), perform the method according to the first embodiment.

Further advantageous embodiments, variations and modifications will be presented in the dependent claims and in the description in combination with the figures.

BRIEF DESCRIPTION OF THE DRAWINGS

The invention will be explained in greater detail with reference to example embodiments depicted in the drawings is appended.

The accompanying drawings are included to provide a further understanding of the present invention and are incorporated in and constitute a part of this specification. The drawings illustrate the embodiments of the present invention and together with the description serve to explain the principles of the invention.

Figure 1:
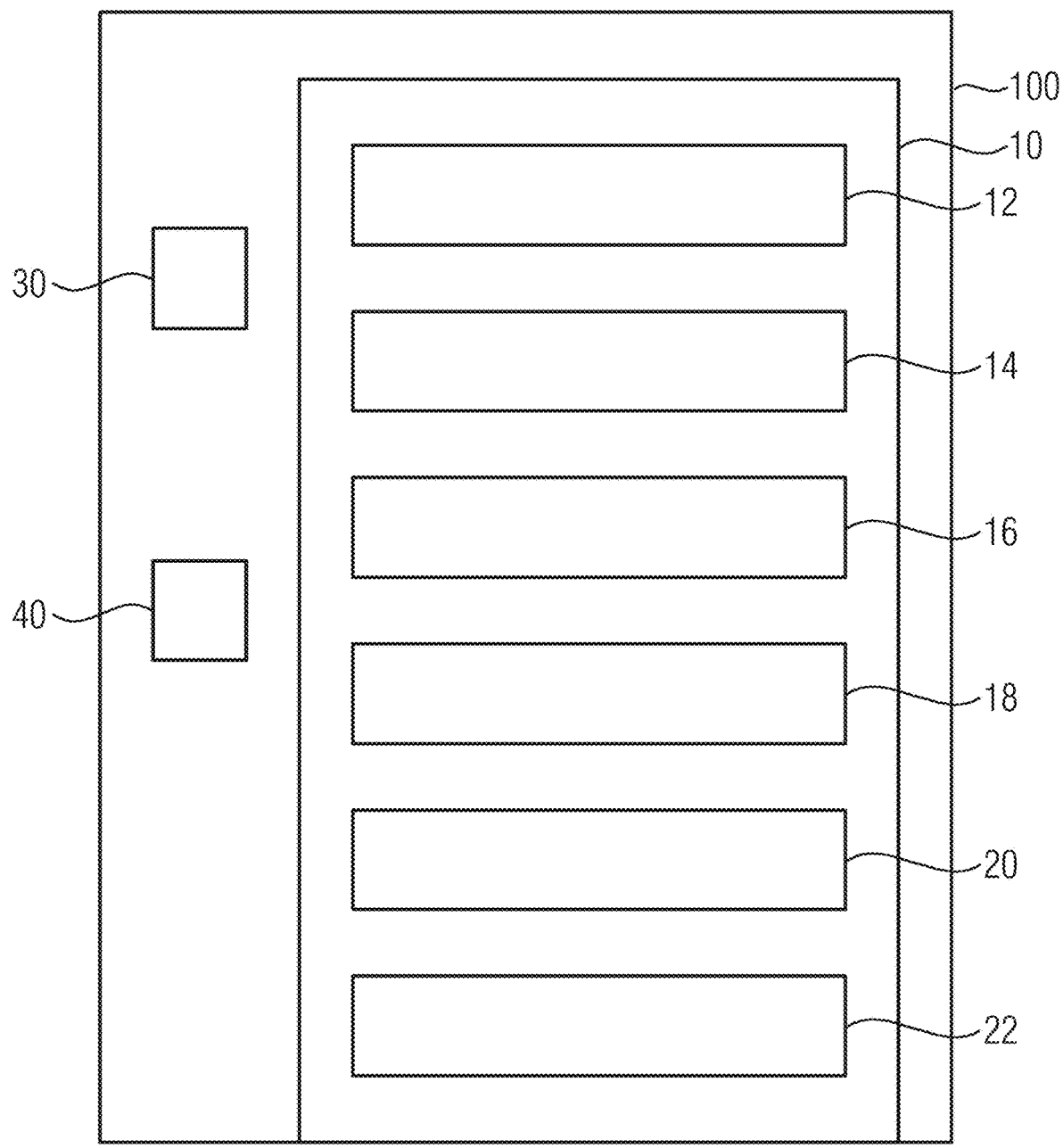

Other embodiments of the present invention and many of the intended advantages of the present invention will be readily appreciated as they become better understood by reference to the following detailed description. The elements of the drawings are not necessarily to scale relative to each other. Like reference numerals designate corresponding similar parts.

Figure 2:
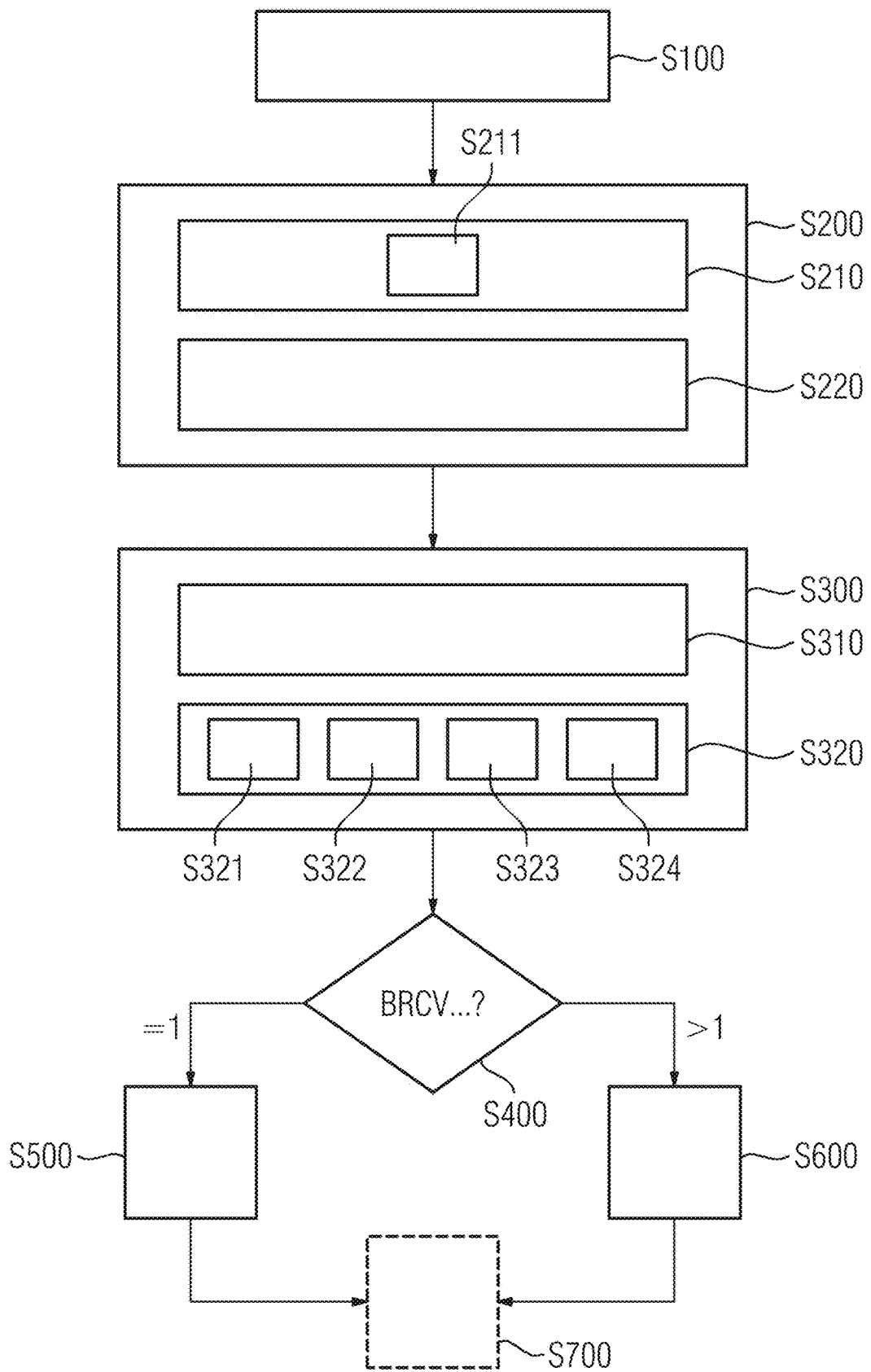
Figure 3:
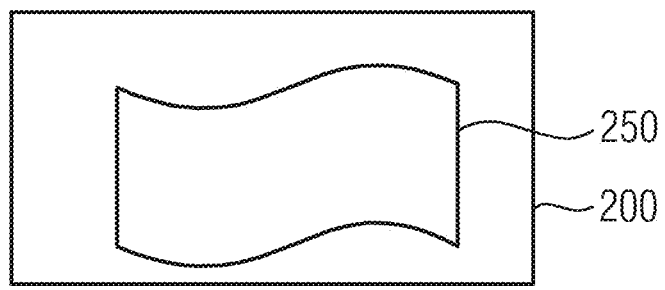
Figure 4:
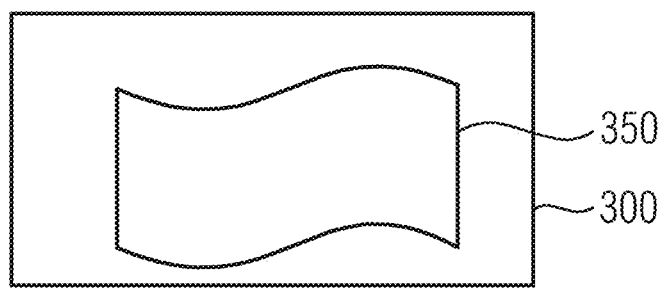

FIG. 1 shows a schematic block diagram illustrating a system for evaluating dose events according to the second embodiment of the present invention;

FIG. 2 shows a schematic flow diagram illustrating a method for evaluating dose events according to the first embodiment of the present invention;

FIG. 3 shows a schematic block diagram of a non-transitory computer-readable storage medium according to the third embodiment of the present invention; and FIG. 4 shows a schematic block diagram of computer program product according to the fourth embodiment of the present invention.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Accordingly, according to a first embodiment of the present invention, a computer-implemented method for evaluating dose events of at least one medical imaging exam is provided, comprising:

receiving at least one list of dose events of the at least one medical imaging exam;

providing a body region counter value indicating a number of body regions;

determining whether the body region counter value is 1 or larger than 1;

associating, when the provided body region counter value is 1, all of the dose events of the at least one list with a standardized body region based protocol identifier;

associating, when the provided body region counter value is larger than 1, each dose event of the at least one list with at least one standardized body region based protocol identifier in such a way that the dose events are associated with a number of different standardized body region based protocol identifiers, wherein the number of different standardized body region based protocol identifiers with which dose events are associated is equal to the provided body region counter value.

All lists of dose events refer to one and the same patient and may therefore also be designated as "patient's exam lists". The patient's exam lists of dose events can, for example, be provided as one or more DICOM files from a single study, especially dose sheets (e.g., black-images), dose reports (e.g., Radiation Dose Structured Reports, RDSRs) and so on.

The standardised body region based protocol identifier in particular is a standardized value or key associated with a certain body region and can more particularly be a RadLex Playbook Identifier (RPID) and/or a LOINC code.

The first embodiment of the present invention therefore advantageously provides an automated software mechanism that allows the comparison and benchmarking of dose values, for example in DICOM objects created by different medical imaging devices, (or: medical scanner devices) by different tenants, in different regions, using different modalities and/or different manufacturer models, using non-standardised different local protocols for specific exams and scans.

The term "tenant", as used herein, indicates an entity such as a specific hospital or a location where, or under the tutelage of which, a specific dose event or a sequence of dose events (exam) has been administered to a patient.

The term "modality", as used herein, refers to a type of the source of medical information about a patient, in particular to a type of medical imaging device, such as a computer tomography (CT) scan, a mammography scan, a molecular imaging (nuclear medicine, NM or positron tomography, PT) scan, x-ray scan and so on. Of course, additional modalities exist such as genetic tests, lab results, questionnaires, blood work and so on but the embodiments of the present invention are focused specifically on medical imaging modalities.

A manufacturer model, as the term is used herein, indicates a specific machine, scanner or device, produced by a specific manufacturer of medical imaging devices. For example, specific computer tomography scanners are the Somatom Force, Somatom Sensation, etc. all registered trademarks, all manufactured by SIEMENS Healthineers (registered trademark).

At least one embodiment of the invention further enables fair and scientifically sound comparison of a used dose for scanners and exams even when the scanner protocols used in the lists of dose events are local and not comparable. Further, at least one embodiment of the invention provides a way to compare dose values from protocols created by scanners from different institutions (tenants) even when they are not operatively connected (e.g. for automatic data exchange).

At least one embodiment of the invention further provides a way to compare dose values from protocols created by different scanners and with different body parts specified for the same examination.

At least one embodiment of the invention further provides a way to compare dose values from protocols created by different scanners and with different exam types (local protocols) specified for the same examined body region.

At least one embodiment of the invention further provides a way to compare dose values from protocols created by different CT scanners and with different body phantom types (e.g., 16 cm/32 cm body phantoms in CT) specified.

Typical CT body phantoms are made of solid acrylic, 15 cm thick, with diameters of 32 cm and 16 cm respectively for body and head. Each phantom e.g. contains five probe holes, one in the center and four around the perimeter, 90° apart and 1 cm from the edge, with five acrylic rods plugging the holes.

One of the main advantages of at least one embodiment of the present invention is that it is checked whether the received at least one list of dose events comprises multiple scans with such properties that groups of dose events can be identified which belong to different body regions of the patient's body. A positive result of this check may be designated as "multi-region TRUE".

Then, region support similar to the previously known exam support can be provided, i.e. known post-exam processing techniques can be applied to the individual groups of dose events (i.e. the body regions) instead of to the entire list of dose events and can therefore be better tailored and suited towards the specific nature of the dose events.

In particular, dose amounts can be accumulated per body region with high accuracy. This means that dose reference values can be efficiently and accurately provided and applied per region, leading e.g. to more accurate dose alerts, as the dose alerts can be generated on a "per region" scope mechanism. Standard protocols can be mapped to regions, providing more accurate data for further processing. Similarly, dose benchmarking can be extended to a "per region" scope.

According to a second embodiment of the present invention, a system for evaluating dose events of at least one medical imaging exam is provided, comprising:

a computing device configured to implement:

an input module configured to receive at least one list of dose events of the at least one medical imaging exam;

a region counter module configured to provide a body region counter value indicating a number of body regions;

a counting module configured to determine whether the body region counter value is 1 or larger than 1; and an associating module, configured to:

associate, when the provided body region counter value is 1, all of the dose events of the at least one list with a standardized body region based protocol identifier; and to associate, when the provided body region counter value is larger than 1, each dose event of the at least one list with at least one standardized body region based protocol identifier in such a way that the dose events are associated with a number of different standardized body region based protocol identifiers, wherein the number of different standardized body region based protocol identifiers with which dose events are associated is equal to the provided body region counter value.

The computing device may be realised as any device for computing, in particular for executing a software, an app, or an algorithm. For example, the computing device may comprise a central processing unit (CPU) and a memory operatively connected to the CPU. The computing device may also comprise an array of CPUs, an array of graphical processing units (GPUs), at least one application-specific integrated circuit (ASIC), at least one field-programmable gate array (FPGA) or any combination of the foregoing.

Some, or even all, modules of the system may be implemented by a cloud computing platform.

In systems based on cloud computing technology, a large number of devices is connected to a cloud computing system via the Internet. The devices may be located in a remote facility connected to the cloud computing system. For example, the devices can comprise, or consist of, equipments, sensors, actuators, robots, and/or machinery. The devices can be medical devices and equipments in a healthcare unit.

The cloud computing system may enable remote configuring, monitoring, controlling, and maintaining connected devices (also commonly known as 'assets'). Also, the cloud computing system may facilitate storing large amounts of data periodically gathered from the devices, analyzing the large amounts of data, and providing insights (e.g., Key Performance Indicators, Outliers) and alerts to operators, field engineers or owners of the devices via a graphical user interface (e.g., of web applications). The insights and alerts may enable controlling and maintaining the devices, leading to efficient and fail-safe operation of the devices. The cloud computing system may also enable modifying parameters associated with the devices and issues control commands via the graphical user interface based on the insights and alerts.

The cloud computing system may comprise a plurality of servers or processors (also known as 'cloud infrastructure'), which are geographical distributed, connected with each other via a network. A dedicated platform (hereinafter referred to as 'cloud computing platform') is installed on the servers/processors for providing above functionality as a service. The cloud computing platform may comprise a plurality of software programs executed on one or more servers or processors of the cloud computing system to enable delivery of the requested service to the devices and its users.

According to a third embodiment of the present invention, a non-transitory computer-readable storage medium is provided that comprises executable program code configured to, when executed (in particular when executed by the system according to the second embodiment of the invention), perform the method according to the first embodiment.

The storage medium may be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Laserdisc, Phasewriter (Phasewriter Dual, PD), Compact Disc (CD), Digital Video Disc (DVD), High Definition DVD (HD DVD), Blu-ray Disc (BD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM) or a data carrier/medium.

According to a possible fourth embodiment of the present invention, a computer program product is provided that comprises executable program code configured to, when executed (in particular when executed by the system according to the second embodiment of the invention), perform the method according to the first embodiment.

According to a possible fifth embodiment of the present invention, a data stream is provided that comprises, or is configured to generate, executable program code configured to, when executed (in particular when executed by the system according to the second embodiment of the invention), perform the method according to the first embodiment.

Further advantageous embodiments, variations and modifications will be presented in the dependent claims and in the description in combination with the figures.

In some advantageous embodiments, the standardized body region based protocol identifiers comprise identifiers for any or all of the following body regions: abdomen, body, bone, breast, cervical spine, chest, extremities, extremity, face, head, lower extremity, lumbar spin, lumbosacral spine, neck, pelvis, skull, skull base to mid-thigh, spine, thoracic spine, thoracolumbar spine, upper extremity, wholebody.

In some advantageous embodiments, providing the body region counter value comprises receiving a user input regarding the body region counter. In this way, an experienced user such a as a physician or a skilled medical technician can directly set the number of body regions of the at least one list of dose events.

In some advantageous embodiments, providing the body region counter value comprises automatically determining the body region counter value based on the at least one list of dose events. In this way, the user is assisted in finding the correct number of body regions. Preferably, automatically determining the body region counter value comprises sequentially investigating the dose events of the at least one list, determining for each individual dose event of the at least one list of dose events whether at least one predetermined criterion is met (or: fulfilled), and increasing the body region counter value by 1 whenever the at least one predetermined criterion is met (or: fulfilled) by an individual dose event.

In some advantageous embodiments, one criterion (e.g. designated as a first criterion) of the at least one predetermined criterion for increasing the body region counter value is whether the currently investigated dose event is a topogram and the directly previously investigated dose event (i.e. the dose event immediately before/above the currently investigated dose event in the list of dose events) was not a topogram. The topogram often acts as a digital overview image in the planning of CT examinations. It is not unusual to perform two topograms in a row, but after the one or two topograms usually one or more detailed scans follow. If after a detailed scan another topogram is performed, this usually indicates that the exam is moving on to a new body region for which a topogram has not yet been produced. This is reflected by the above criterion.

In some advantageous embodiments, one criterion (e.g. designated as a second criterion) of the at least one predetermined criterion for increasing the body region counter value is whether a body phantom type set for the currently investigated dose event has a size different from (in particular: is smaller than) the size of a body phantom type set for the directly previously investigated dose event. Usually, smaller body phantoms are set for either for exams on children or for exams on the head of an adult. In the case of children, the body phantom type will generally stay the same, i.e. at 16 cm. Thus a change of the size of the set body phantom type only occurs for adults and then usually indicates a change in the body region to be examined (from a smaller one to a larger one or the other way around). The body part may be indicated e.g. by a field of a DICOM file.

In some advantageous embodiments, one criterion (e.g. designated as a third criterion) of the at least one predetermined criterion for increasing the body region counter value is whether a dose length product (e.g. DLP dose value in CT in mGy·cm) of the currently investigated dose event is higher than a predetermined value which is preferably 130 mGy*cm or above (more preferably between 150 mGy*cm and 200 mGy*cm, most preferably 180 mGy*cm), while a body part of the currently investigated dose event is different from a body part of the directly previously investigated dose event. This criterion reflects that it is unusual for body parts that lie within the same body region to be subjected to high DLP values.

Any single, any combination, or all of the above criteria may be used in embodiments of the present invention. A combination of the second and third criterion is particularly preferred. It shall be understood that additional criteria may be defined, e.g. criteria reflecting additional knowledge about indicators of changes in the currently examined body region during an exam. Although the criteria are at times designates as first, second and third criterion or as criterion 1, criterion 2, criterion 3 and so on, it should be understood that this should serve only to better distinguish the criteria from one another and does specifically not indicate any order or priority among these criteria.

In some advantageous embodiments, the associating of the dose events with the standardized body region based protocol identifiers is based on at least one data field of property files of the dose events. The property files are preferably data files that describe one or more properties of at least the dose events in a standardized format and are more preferably DICOM (registered trademark) files. Data fields (so-called "tags") of the DICOM files comprise information e.g. about an anatomical focus of a dose event and may therefore comprise hints as to which body region the corresponding dose event should be associated with.

In some advantageous embodiments, a plurality of lists of dose events is received (for example caused by so called split exams at the scanner device while the exam is running and distribution of the split exams for tele radiology where the individual radiologist is reading one split exam and sends the exam back to the PACS system from where the exam (and its split child exams) is retrieved to perform dose analysis). Such events are also designated as "multi-study events" or as "multi-study true" events.

Especially in that case (but not necessarily limited thereto), the method may further comprise:

checking whether at least two of the received plurality of lists of dose events relate to the same real-world medical imaging exam; and modifying the lists such that no real-word dose event is contained more than once in the plurality of lists of dose events.

In this way, it is ensured that no real-world dose event is counted more than once when accumulating the dose values of dose events associated with each standardized body region based protocol identifier for the purpose of comparison to a dose reference value for that body region.

The term "real-world" here refers to an actual exam having been physically performed on an actual patient, as opposed to e.g. a mere duplication of data, a merely planned exam, a simulated exam, and so on. The term "real-world" exam could thus also be replaced by the term "physical exam". A "real-wold" dose event thus in particular indicates an actual dose event which has affected an actual patient, as opposed to e.g. a mention of the same dose event in a duplicate of the original list.

It should also be understood that the steps described in the foregoing and in the following regarding the multi-study event case describe a method for removing duplicate lists of dose events which can also be performed independently from the steps described in the foregoing with respect to the determining of the body region counter value and/or the associating of the dose events with standard protocol based body region identifiers.

For example, the method of removing duplicate lists of dose events may be applied to a picture archiving system (PACS), e.g. in regular intervals such as every night, to ensure that no duplicate lists of dose events are present in the PACS. Alternatively or additionally, the method of removing duplicate lists of dose events may be applied whenever a plurality of lists of dose events is retrieved from the PACS, for instance in response to a query.

In some advantageous embodiments, checking whether at least two of the received plurality of lists of dose events relate to the same real-world medical imaging exam comprises comparing at least one of the following parameters between the at least two lists:

a modality used to perform dose events;
a manufacturer of a medical imaging device used to perform dose events;
a medical imaging device type;
a medical imaging device ID (e.g., a serial number);
a patient ID of a patient;
a study date;
a tenant ID of a tenant;
depending on the modality, a total (or: accumulated) dose value or a total (or: accumulated) scan duration.

For example, in the case of a magnetic resonance scanner (MR), a scan duration may be compared as one of the parameters, whereas in the case of e.g. fluoroscopy (RF), mammography (MG), computer tomography (CT), angiography (XA), or radiography (XR), dose values may be compared as one of the parameters.

The format, dimension or unit in which the accumulated dose value is given and/or calculated may depend on the modality. For a computer tomography scanner (CT) as modality, the dose value is preferably given and/or calculated in the dose length product, DLP. For a mammography scanner (MG), the dose value is preferably given and/or calculated in the average glandular dose (AGD).

For other modalities like x-ray scanners (XR), the dose value is preferably given and/or calculated in the dose area product (DAP). The dose area product is defined as the absorbed dose multiplied by the area irradiated, conventionally expressed in gray-centimetres squared.

In some advantageous embodiments of the second embodiment of the present invention, the computing device is further configured to implement a checking module configured to:

check whether at least two of the received plurality of lists of dose events relate to the same real-world medical imaging exam; and preferably modify the lists such that no real-word dose event is contained more than once in the plurality of lists of dose events.

In some variants, the checking module may perform the checking of whether at least two of the received plurality of lists of dose events relate to the same real-world medical imaging exam after the body region counter value has been determined. The checking module may be configured to prevent the associating of duplicated dose events with standard protocol based body region identifiers. In other words, the checking module may be configured to ensure that each real-world dose event is only once associated with any particular standard protocol based body region identifier. Moreover, the system may also be provided without the checking module.

In some advantageous embodiments, checking whether at least two of the received plurality of lists of dose events relate to the same real-world medical imaging exam comprises comparing at least one of the following parameters between the at least two lists:

a modality used to perform dose events;
a manufacturer of a medical imaging device used to perform dose events;
a medical imaging device type;
a medical imaging device ID;
a patient ID of a patient;
a study date;
a tenant ID of a tenant;
depending on the modality, a total (or: accumulated) dose value or a total (or: accumulated) scan duration.

It should be understood that the system according to the second embodiment of the present invention may be modified and adapted according to any option, modifications and embodiments described for the method according to the first embodiment of the present invention, and vice versa.

FIG. 1 shows a schematic block diagram illustrating a system 100 for evaluating dose events of at least one medical imaging exam according to the second embodiment of the present invention.

The system 100 comprises a computing device 10 configured to implement at least an input module 12, a region counter module 14, a counting module 16 and an associating module 18.

The computing device 10 may comprise a central processing unit (CPU) and a memory operatively connected to the CPU. The computing device may also comprise an array of CPUs, an array of graphical processing units (GPUs), at least one application-specific integrated circuit (ASIC), at least one field-programmable gate array, or any combination of the foregoing.

Some, or even all, modules of the system may be implemented by a cloud computing platform. In particular, all of the described modules may be provided as a web application run by a cloud computing platform.

The input module 12 is configured to receive at least one list of dose events of at least one medical imaging exam. The at least one list may be provided as one or more DICOM files from a single study, especially dose sheets (e.g., black-images), dose reports (e.g., Radiation Dose Structured Reports, RDSRs) and so on. The input module 12 may be operatively connected to a Picture ArChiving System (PACS) and receive the at least one list of dose events from the PACS.

The PACS, in turn, may be operatively connected to at least one modality, in particular to at least one medical imaging device, and may be configured to automatically receive and/or retrieve data, in particular medical imaging data and/or the at least one list of dose events, from the at least one medical imaging device and store (or: archive) them. In some advantageous embodiments, the system 100 may comprise a PACS and/or the at least one modality operatively connected to the PACS.

An example of a received list of dose events, here in the form of a dose protocol (or: dose sheet), is given in the following Table 1:

TABLE 1 first example list, comprising nine dose events

| Total mAs 9117 | | Total DLP 2045 mGy * cm | | DLP | | |
|---|---|---|---|---|---|---|
| Patient Position H-SP | Scan | kV | mAs/ ref. | $CTDI_{vol*}$ mGy | mGy * cm | TIs | cSL mm |
| Topogram | 1 | 120 | 59 mA | 0.49 S | 20 | 4.2 | 0.6 |
| Topogram | 2 | 120 | 59 mA | 0.49 S | 21 | 4.3 | 0.6 |
| Head | 3 | 120 | 330/350 | 50.40 S | 872 | 1.0 | 0.6 |
| C_Spine | 4 | 120 | 262/210 | 17.72 L | 380 | 1.0 | 0.6 |
| Topogram | 5 | 120 | 35 mA | 0.14 L | 10 | 7.5 | 0.6 |
| PreMonitoring Contrast | 6 | 120 | 20 | 1.20 L | 1 | 0.5 | 10.0 |
| Monitoring | 7 | 120 | 20 | 1.20 L | 1 | 0.5 | 10.0 |
| Art Chest | 8 | 100 | 190/148 | 7.83 L | 381 | 0.5 | 0.6 |
| PV Abdomen | 9 | 100 | 188/248 | 7.76 L | 359 | 0.5 | 0.6 |

| Medium | Type | Iodine Conc. mg/ml | Volume ml | Flow ml/s | CM Ratio |
|---|---|---|---|---|---|
| Contrast | Omnipaque | 300 | 70 | 3.4 | 100% |

Table 1 shows a dose protocol of a CT examination with nine (see numbers in second column) individual scans (see acquisition-protocol names in first column), each generating (or, interpreted in a different way, equal to, or representing) a dose event with an according=$I_{vol}$ (fifth column) and DLP value (sixth column) which are usable to be compared to dose reference values in order to create a dose alert, if necessary.

The CT dose index (CTDI) is a standardized measure of a radiation dose output of e.g. a CT scanner which allows comparing radiation output of different devices. $CTDI_w$ (sometimes also written as CTDIw) is the weighted average of dose across a single scan slice. $CTDI_{vol}$ (sometimes also written as $CTDI_{vol}$) is obtained by dividing $CTDI_w$ by a pitch factor.

The also commonly used dose length product (DLP) factors in the length of the scan to show an overall dose output, i.e., DLP: $CTDI_{vol}$ times scan length.

According to the prior art, protocol standards would advise using the complete exam according to the list of Table 1 for protocol mapping, i.e. associating the entire list with a single standardized body region based protocol identifier, e.g. a RadLex Playbook Identifier (RPID).

However, the example of Table 1 shows that the individual dose events are applied to actually different body regions and that therefore no single dose reference value should be provided for the entirety of the nine dose events in the list.

Rather, one may note that the first three dose events (numbers 1 through 3 in the second column) have been applied to a "head" body region, as is also visible from the small body phantom size type set (key letter "S" for "Small", i.e. 16 cm, in fifth column). One may further note that for the remaining scans (number 4 through 9 in the second column) a large body phantom size type has been set (key letter "L" for "Large", i.e. 32 cm, in fifth column), and that the scan names in the first column refer to body parts different from the head, e.g. "chest" or "abdomen".

The region counter module 14 is configured to provide a body region counter value indicating a number of body regions. The region counter module 14 may be configured to receive a user input regarding the body region counter.

The system 100 may comprise a user interface 30 configured to receive said user input. The user interface 30 may be realized as any, or any combination, of: a mouse, a key-board, a display, a touch screen, or any other known input device.

Advantageously, the user interface 30 is at least partially implemented by a local device and/or a web interface comprising a graphical user interface (GUI). For example, a physician or medical technician may use a desktop PC to open a web interface connected to the computing device 10 implemented by a cloud computing platform, and enter the user input into the web interface.

The web interface implementing the GUI may for example be provided by a server 40 of a service provider which may be part of the system 100. Both the user interface 30 and the server 40 may repeatedly interact and communicate with the computing device 10. For example, the computing device 10 can be implemented by a cloud computing platform, the user interface 30 (e.g. a so-called appliance) may be arranged at the premises of a tenant, and the server 40 may be arranged at the premises of a digital services provider.

In a simple case the user input may directly indicate the body region counter value. For example, a physician or medical technician could use his experience to determine that the list of dose events e.g. of Table 1 comprises three different body regions (a head region, a spine region, and a chest/abdomen region), and therefore directly enter a body region counter value of 3 into the user interface 30.

The region counter module 14 may, additionally or alternatively, be configured to automatically determine the body region counter value based on the at least one list of dose events.

Preferably, automatically determining the body region counter value comprises the optional steps:
initializing the body region counter value with a starting value (e.g. 0 or 1),
sequentially investigating the dose events of the at least one list,
determining for each individual dose event whether at least one predetermined criterion is met, and
increasing the body region counter value by 1 whenever the at least one predetermined criterion is met by an individual dose event.

Optionally, the region counter module 14 may be configured to first determine whether or not a body region counter value of larger than 1 is to be expected or not, and to start the automatically determining of the body region counter value only when it is expected that the body region counter value will be larger than 1.

For example, the region counter module 14 may be configured to expect a body region counter value of larger than 1 when the total DLP value of all dose events of the at least one list is larger than a predetermined threshold, e.g. larger than 2000 mGy*cm. Another criterion for the region counter module 14 to expect a body region counter value of larger than 1 could be when the scan names (or: acquisition-protocol names) in the first column in Table 1 comprise more than one body region name.

Another criterion for the region counter module 14 to expect a body region counter value of larger than 1 would be when the at least one list comprises more than one study (split study caused e.g. by the scanner, so-called Multi-Study), and/or when one or more duplicates of the same list is/are provided.

In this case the analysis of characteristic images of each series (to get information of DICOM tags like Series-Description or Body-Part) of the exam has to be applied through all available split studies of the exam because the content of the image series within the split studies might be disjunct and only their split dose reports have the same content.

In other embodiments, the region counter module 14 may be configured to automatically determine the body region counter value in every case, without first determining an expectation for it.

Preferably, one criterion (hereafter: "criterion 1") for increasing the body region counter value is whether the currently investigated dose event is a topogram and the directly previously investigated dose event was not a topogram.

Advantageously, one criterion (hereafter: "criterion 2") for increasing the body region counter value is whether a body phantom type set for the currently investigated dose event has a smaller cross-section than a body phantom type set for the directly previously investigated dose event.

Preferably, one criterion (hereafter: "criterion 3") for increasing the body region counter value is whether a dose length product of the currently investigated dose event is higher than a predetermined value which is preferably 130 mGy*cm or above, while a body part of the currently investigated dose event is different from a body part of the directly previously investigated dose event. The predetermined value may be between 130 mGy*cm and 200 mGy*cm (both included), preferably between 150 mGy*cm and 190 mGy*cm, both included, especially preferably at 180 mGy*cm.

For the present illustrative example with respect to Table 1, only the criterion 2 and the criterion 3 shall be applied, and the predetermined value shall be set to 180 mGy*cm. It should be understood that any other criteria, or combinations of criteria, can be applied and that the list and examples shown and described herein may also be evaluated in other ways.

For example, referring again to Table 1, first the body region counter value would be set to a starting value, e.g. 1. Then, the listed dose events would be investigated sequentially, starting with the first dose event.

In Table 1, the first dose event meets neither criterion 2 nor criterion 3. Therefore, the body region counter value remains at its starting value of 1.

The second dose event does not meet any of the two chosen criteria either. The body region counter value therefore stays at 1 and the investigation is moved to the third dose event.

The third dose event ("Head") does not meet any of the two chosen criteria, so the body region counter value stays at 1 and the investigation is moved to the fourth dose event. Topograms are a kind of overview scan and are therefore preferably not deemed to be associated with any particular body region, also because the dose amount deposited by a topogram is in most cases small. However, in some variants topograms may be associated with a body region, e.g. by a database.

The fourth dose event ("C_Spine") meets at least criterion 3, because its DLP of 380 mGy*cm is larger than the predetermined value (here: 180) and its body part (spine, e.g. determined based on the acquisition-protocol names of the scans) is different from the body part of the directly previously investigated body part ("head"). Consequently, the body region counter value is increased by 1 (from 1 to 2) and the investigation is moved to the fifth dose event.

In order to evaluate criterion 3, i.e. in order to determine which body part a scan of the list refers to, a database may be used in which each acquisition-protocol name (first column in Table 1) is associated either with no body part (neutral, e.g. topogram) or with one specific body part (e.g. "head"). Alternatively or additionally, the acquisition protocol names themselves may be evaluated, for example by a trained artificial neural network.

Alternatively or additionally, the body regions can be derived from a single characteristic image and/or specific DICOM tags (e.g. Series-Description, Body-Part, etc.) from each available series of images of each scan (i.e. dose event) as part of the exam and provided as a sequence for the complete exam (list of dose events) in a way comparable to the acquisition-protocol names of the scans in the first column of the example lists (tables).

The fifth dose event ("topogram") does not meet any of the two set criteria. The sixth and seventh events are indicating contrast usage but do not contribute much on dose or body regions. Accordingly, throughout the fourth through seventh dose events, the body region counter value remains at 2.

The eighth dose event ("Art Chest") meets at least criterion 3, because its DLP of 381 mGy*cm is larger than the predetermined value (here: 180 mGy*cm) and its body part ("chest") is different from the body part of the directly previously investigated body part ("spine"). Consequently, the body region counter value is increased by 1 (from 2 to 3) and the investigation is moved to the ninth dose event.

The ninth dose event ("PV Abdomen") meets at least criterion 3, because its DLP of 359 mGy*cm is larger than the predetermined value (here: 180) and its body part ("abdomen") is different from the body part of the directly previously investigated body part ("chest"). Consequently, the body region counter value is increased by 1 (from 3 to 4) and the investigation is stopped because of no further dose event (scan) is available, so the total body region counter value remains at 4.

Referring back to FIG. 1, the counting module 16 is configured to determine whether the body region counter value is 1 or larger than 1.

In the example of Table 1, the counting module 16 would determine that indeed the body region counter value is larger than 1 (namely 3).

The associating module 18 is configured to perform different actions depending on the result of the counting module 16.

The associating module 18 is configured to, when the provided body region counter value is 1, associate all of the dose events of the list with a single standardized body region based protocol identifier, for example with a single RPID and/or a single LOINC code.

The associating module 18 is further configured to, when the provided body region counter value is larger than 1, associate each dose event of the at least one list with at least one standardized body region based protocol identifier (e.g. a RPID or a LOINC code) in such a way that the dose events are associated with a number of different standardized body region based protocol identifiers equal to the provided body region counter value. In other words, after it has been determined that there are four body regions, the dose events are sorted into the four body regions.

In the present example, the associating module 18 would therefore associate the nine dose events with three different standardized body region based protocol identifiers.

The associating module 18 may first acquire, or determine, which dose event belongs to which of the three body regions (since the number of body regions is equal to the determined body region counter value).

In a simple variant, the user may, e.g. via the user interface 30, group the dose events manually into a number of groups equal to the body region counter value. For example, the user interface 30 could, in a graphical user interface (GUI), indicate the list of dose events as well as the determined (or input) body region counter value, and prompt (and/or guide) the user to group the dose events into a number of groups equal to the body region counter value.

The system 100, in particular the computing device 10, may instruct the user interface 30 and the GUI to display recommendations for the grouping to the user which the user may then accept or alter, using e.g. their own experience. The system 100 may even be configured such that the user may not change the recommendations for the grouping by the system 100, although usually it will be desired to allow the user to override the automatic determinations of the system 100.

For the recommendations, the computing device 10 may comprise a grouping module 20 configured to group all those dose events into the same group for which the body region counter value was the same.

In the example of Table 1, for the first three dose events (1 through 3) the body region counter value ended up being 1 so they are grouped into a first group. For the fourth dose event, the body region counter value ended up being 2 so it is grouped into its own, second group. Additionally, for the fifth through the eighth dose event (5 through 8), the body region counter value ended up being 3 so that they would be grouped into a third group.

Finally, for the ninth dose event (9), the body region counter value ended up being 4 so that it would be grouped into a fourth group.

Four groups would then have been determined:

Group 1 comprises dose events 1 through 3 (Topogram, Topogram, Head)

Group 2 comprises dose events 4 through 7 (C_Spine, Topogram, PreMonitoring, Monitoring)

Group 3 comprises dose event 8 (Art Chest) Group 4 comprises dose event 9 (PV Abdomen) Evidently, the groups 1 through 4 already correspond to separate body regions.

The associating module 18 will then determine a standardized body region based protocol identifier (e.g. RPID, LOINC code etc.) for each of the determined groups, i.e. for each group individually, but jointly for all of the dose events in each group.

For associating the groups with standardized body region based protocol identifiers (or, in other words, with body regions), known algorithms for associating entire exams with standardized body region based protocol identifiers may be used. For example, methods as applied by the American College of Radiology (ACR) Dose Index Registry may be applied for the associating (or: "mapping") of dose events with standardized body region based protocol identifiers (or: "standard protocols"), see, e.g., the Dose Index Registry user documentation.

Specifically, any or all tags (e.g. RadLex IDs, RIDs) within DICOM files of the dose events may be evaluated in order to find the best fitting standardized body region based protocol identifier for all dose events within one and the same group.

In the above example, group 1 is associated with a standardized body region based protocol identifier for a "Head" body region, group 2 is associated with a standardized body region based protocol identifier for a "Spine" body region and group 3 is associated with a standardized body region based protocol identifier for an "Chest" body region and group 4 is associated with a standardized body region based protocol identifier for "Abdomen".

Completing the example, for the four identified groups (regions) the automated standard protocol mapping would give the following four standard mapping results of the RadLex Playbook for the entire exam (in contrast to only the first mapping result of group 1 (CT Head wo—RPID22) if multi-region detection & mapping algorithm according to the present invention would not have been available):

Group 1 comprises dose events 1 through 3 (Topogram, Topogram, Head)
→CT Head wo (RPID22)
Group 2 comprises dose event 4 through 7 (C_Spine, Topogram, PreMonitoring, Monitoring)
→CT C-Spine wo (RPID19)
Group 3 comprises dose event 8 (Art Chest)
→CT Chest w (RPID18)
Group 4 comprises dose events 9 (PV Abdomen)
↓CT Abd w (RPID5)

The following Table 2 shows another example.

TABLE 2 second example list, comprising four dose events

Total mAs 7513

Patient    Total DLP 1991 mGy * cm

| Position H-SP | Scan | kV | mAs/ ref. | CTDI$_{vol}$ * mGy | DLP mGy * cm | TIs | cSL mm |
|---|---|---|---|---|---|---|---|
| Topogram | 1 | 80 | 19 mA | 0.05 S | 1 | 27 | 0.6 |
| Head | 2 | 120 | 256/300 | 48.12 S | 831 | 1.0 | 0.6 |
| Topogram | 3 | 120 | 59 mA | 0.24 L | 18 | 7.8 | 0.6 |
| Right Femur | 4 | 140 | 200/146 | 19.71 L | 1141 | 0.5 | 0.6 |

In the example of Table 2, when e.g. criterion 1 is applied, the body region counter value will be determined to be 2, because dose events 1 and 3 fulfil at least criterion 1 as explained above. When criterion 1 is applied, the starting value for the body region counter value is advantageously set to 0, since the first scan typically is a topogram.

Accordingly, two groups will be automatically determined, and the dose events will be associated with the corresponding standardized body region based protocol identifiers: group 1 (body region "Head") consisting of dose events 1 and (Topogram, Head), and group 2 (body region "Right Femur") consisting of dose events 3 and 4 (Topogram and right Femur).

The following Table 3 shows yet another example.

TABLE 3 third example list, comprising seven dose events

Total mAs 9117

Patient    Total DLP 2045 mGy * cm

| Position H-SP | Scan | kV | mAs/ ref. | CTDI$_{vol}$ * mGy | DLP mGy * cm | TIs | cSL mm |
|---|---|---|---|---|---|---|---|
| Topogram | 1 | 130 | | 0.08 (L) | 8.16 | 8.2 | 0.6 |
| Pre-monitoring I.V. Bolus | 2 | 130 | 20 | 2.08 (L) | 2.08 | 0.6 | 5.0 |
| Monitoring | 3 | 130 | 20 | 2.08 (L) | 2.08 | 0.6 | 5.0 |
| Th/OBB KM | 4 | 130 | 60/70 | 6.72 (L) | 304.95 | 0.6 | 1.2 |
| Abd. KM pv | 5 | 130 | 102/120 | 11.48 (L) | 579.18 | 0.6 | 1.2 |
| Topogram | 6 | 130 | | 0.08 (L) | 4.24 | 3.4 | 0.6 |
| Neck | 7 | 130 | 150/100 | 18.70 (L) | 404.51 | 1.0 | 0.6 |

In the example of Table 3, when e.g. criteria 1 and 3 are applied (and the starting set value is set to 0), the body region counter value will be determined to be 3, because dose events 1 and 6 fulfil at least criterion 1 and dose event 5 fulfils at least criterion 3 as explained above.

Accordingly, three groups will be automatically determined, and the dose events will be associated with the corresponding standardized body region based protocol identifiers: group 1 (body region "Thorax") consisting of dose events 1 through 4 (Topogram, Premonitoring, Monitoring, Th/OBB KM, Abd. KM pv), group 2 (body region "Abdomen") consisting of dose event 5 and group 3 (body region "Neck") consisting of dose events 6 and 7 (Topogram and Neck).

Referring again to FIG. 1, the system 100 may further comprise an optional checking module 22 that is run (at least) when a plurality of lists of dose events (for example in the "Multi-Study" case, meaning that a single real-world exam has been split into different studies all containing the same dose information but different sets of series with images) is received by the input module 12. The checking module 22 may be configured to:

check whether at least two of the received plurality of lists of dose events (see definition above) relate to the same real-world medical imaging exam; and modify the plurality of lists such that no real-word dose event is contained more than once in the plurality of lists of dose events (see definition above).

For example, a single real-world exam on a patient may comprise, as discussed above, scans of a plurality of body regions, collected in a study which receives a unique study instance unique identifier (StudyInstanceUID). A tenant, or a physician, may decide to duplicate the study, for example in order to send the duplicates to different experts so that the scans (dose events) for each body region may be evaluated by a different, corresponding expert.

Duplicating the study may, however, result in the duplicate studies acquiring their own different StudyInstanceUIDs. The result is that, even though no additional real-world exam has been performed, a plurality of seemingly unique studies (i.e. same lists of dose events) with different StudyInstanceUIDs now exists which normally indicates that different exams have been performed. The existence of duplicates makes correct comparisons of actual real-world applied doses with the corresponding reference values less accurate as duplicates will increase the formally accumulated applied dose amount counterfactually.

Additionally, the plurality of different studies may contain the same dose information (list or lists of dose events) in each of the duplicates but the series with images (belonging to the study that comprises the list or lists of dose events) might be disjunct across the duplicates such that the studies have only such series with images available that a particular expert needs (e.g. head images for a radiologist specialized in heads etc.). All other series with images might be removed from a single duplicate. For this reason, in case of duplicated exams the mapping algorithm advantageously navigates to individual duplicated studies in order to get the body region information needed for mapping. This is not needed in case duplication has not happened because then all series with all images are available in the single study.

The checking module 22 is therefore optionally provided to eliminate duplicate lists that have no own real-world basis.

Specifically, the checking module 22 may be configured to determine, for each pair of lists within the received plurality of lists of dose events (see definition above) that have different StudyInstanceUIDs, whether the two lists indicate the same parameter values for all parameters of a predefined set of parameters.

The predefined set of parameters may include any or all of the following:
a modality (e.g. CT),
a manufacturer of the medical imaging device,
a medical imaging device model
a medical imaging device ID (e.g. scanner hash, unique equipment hash, device serial number),
a patient ID
a study date (e.g. Mar. 26, 2018)
a tenant ID;
depending on the modality, a total (or: accumulated) dose value or a total (or: accumulated) scan duration.

The checking module 22 is further configured to discard a copy of the two lists of dose events when all of the parameters values of the parameters of the predefined set of parameters are equal.

Preferably, the values of all of the above parameters (modality, manufacturer, scanner ID, patient ID, study date, medical imaging device model, tenant ID and total dose value) are compared (i.e. are included in the predefined set of parameters) such that only when all of these parameter values are equal for two lists is one of the two lists discarded (e.g. the list with the higher/newer StudyInstanceUID) as a duplicate. If a specific study has been duplicated more than once, as many studies as necessary will be discarded until only one original remains.

The checking module 22 may e.g. be configured to run in fixed intervals, e.g. every night. The checking module 22 helps to deal with the so-called race condition where executables running in parallel access a study and thereby potentially create an undesired duplicate. The checking module 22 makes it unnecessary to e.g. lock specific data stores so that they can only be accessed by one executable at the time, or to work with shared data between running executables running concurrently e.g. as cloud computing services.

FIG. 2 shows a schematic flow diagram illustrating a method for evaluating dose events of at least one medical imaging exam according to the first embodiment of the present invention.

The method of FIG. 2 may be performed using the system according to the first embodiment of the present invention, in particular using the system 100 according to FIG. 1. Accordingly, the method of FIG. 2 may be adapted, modified and varied according to any of the options, embodiments and examples described with respect to the system according to the first embodiment (in particular the system 100) and vice versa.

For the purpose of explanation, the method of FIG. 2 will be described also using reference signs shown in FIG. 1. However, this is mainly for the sake of improved intelligibility and should not be interpreted to mean that the method of FIG. 2 may only be performed by the system 100, or that the system 100 of FIG. 1 may only function by performing the steps of FIG. 2.

In a step S100, at least one list of dose events of at least one medical imaging exam is received, e.g. as has been described in the foregoing with respect to the input module 12 implemented by the computing device 10 of the system 100. For example, a patient may be selected in a user interface 30 with the intention of finding accumulated dose values for that patient.

As a result of the selection, a query may be sent from the user interface 30 to a data repository, e.g. a Picture Archiving System, PACS, for data pertaining to that patient. The at least one list of dose events may then be retrieved from the data repository. The list may be of the form as shown in the above examples in Table 1 to Table 3, or in a similar form.

In an optional step S200, it is ensured that no undesired duplicates without real-world basis are present in the at least one list of dose events, e.g. as has been described in the foregoing with respect to the checking module 22 implemented by the computing device 10 of the system 100. In some embodiments, step S200 may be left out. In other embodiments, step S200 may be always performed. In still other embodiments, step S200 may be performed always when a plurality of lists of dose events is received in step S100. Step 200 is especially advantageous in the multi-study case.

Step S200 may comprise a step S210 of checking whether at least two of the received plurality of lists of dose events relate to the same real-world medical imaging exam, and a step S220 of modifying the received lists such that no real-word dose event is contained more than once in the plurality of lists of dose events (see definition above).

The step S210 may comprise a step S211 of determining, for each pair of lists within the received plurality of lists of dose events that have different StudyInstanceUIDs, whether the two lists indicate the same parameter values for all parameters of a predefined set of parameters.

The set of parameters may include any or all of the following:
a modality (e.g. CT),
a manufacturer of the medical imaging device,
a medical imaging device model
a medical imaging device ID (e.g. scanner hash, unique equipment hash, device serial number),
a patient ID
a study date (e.g. Mar. 26, 2018)
a tenant ID;
depending on the modality, a total (or: accumulated) dose value or a total (or: accumulated) scan duration.

Preferably, the set of parameters comprises all of the above parameters.

In step S220 then lists of the received plurality of lists of dose events are discarded such that, of all lists that have different StudyInstanceUIDs but are equal in all values of the parameters of the predefined set of parameters, only one list is kept.

After the plurality of lists of dose events that is to be evaluated has been finalized (either by using all of the lists received in step S100 without performing step S200, or by using all of the remaining lists after step S200 has been performed), in a step S300 a body region counter value indicating a number of body regions is provided. The body region counter value may specifically be provided as has been described in the foregoing with respect to the region counter module 14 implemented by the computing device 10 of the system 100.

Thus, step S300 may comprise a step S310 of receiving a user input regarding the body region counter, preferably receiving a user input indicating the body region counter value itself, and/or the step S300 may comprise a step S320 of automatically determining the body region counter value based on the at least one list of dose events.

The step S320 of automatically determining the body region counter value preferably comprises, after initializing S321 the body region counter value at 0, sequentially investigating S322 the dose events of the at least one list, determining S323 for each individual dose event whether at least one predetermined criterion is met, and increasing S324 the body region counter value by 1 whenever the at least one predetermined criterion is met by an individual dose event.

Especially preferably, the three criteria as described in the foregoing with respect to the region counter module 14 are used in step S323.

In other words: one criterion ("criterion 1") for increasing S324 the body region counter value is whether the currently investigated dose event is a topogram and the directly previously investigated dose event was not a topogram.

Another criterion ("criterion 2") for increasing S324 the body region counter value may be whether a body phantom type set for the currently investigated dose event has a smaller cross-section than a body phantom type set in the directly previously investigated dose event.

Another criterion ("criterion 3") for increasing S324 the body region counter value may be whether a dose length product, DLP, of the currently investigated dose event is higher than a predetermined value which is preferably 130 mGy*cm or above, while a body part of the currently investigated dose event is different from a body part of the directly previously investigated dose event. The predetermined value may be between 130 mGy*cm and 200 mGy*cm (both included), more preferably between 150 mGy*cm and 200 mGy*cm, both included, especially preferably at 180 mGy*cm.

In a step S400, it is determined whether the body region counter value, BRCV, after it has been finalized in step S300, is equal to 1 (=1) or whether it has a value larger than 1 (>1).

If the body region counter value, BRCV, is determined in step S400 to be equal to 1 (left branch in FIG. 2), then, in a step S500, all of the dose events of the list are associated with a single standardized body region based protocol identifier, e.g. a RadLex Playbook identifier (RPID), a LOINC ID and/or the like.

Associating with a single standardized body region based protocol identifier means that, from any specific ontology, only one single body region based protocol identifier is selected and associated with the entirety of the dose events. Still, the dose events may be associated with multiple body region based protocol identifiers, each one from a different ontology. For example, all of the dose events may be associated with one body region based protocol identifier from the RadLex ontology, one LOINC code, and so on.

The associating S500 of the dose events with a body region based protocol identifier may be performed according to any of the options and variations described in the foregoing with respect to the associating module 18 implemented by the computing device 10 of the system 100.

If the body region counter value, BRCV, is determined in step S400 to be large than 1 (right branch in FIG. 2, ">1"), then, in a step S600, each dose event of the at least one list is associated with at least one standardized body region based protocol identifier in such a way that the dose events are associated with a number of different standardized body region based protocol identifiers equal to the provided body region counter value.

Step S600 means that, effectively, the list of dose events is split up into smaller parts (groups corresponding to the determined body regions), and each group can advantageously be treated as a separate exam (or sub-examination) of its own right, preferably with all consequences like reference value mapping, standard protocol mapping as well as dose alert creation.

The step S600 may be performed according to any of the options and variations described in the foregoing with respect to the associating module 18 implemented by the computing device 10 of the system 100.

After step S500 and/or after step S600, one or more optional step(s) S700 may be performed in which the results of steps S500 and/or step S600, respectively, are processed. In particular, all of the dose values of all dose events associated with each specific standardized body region based protocol identifier (i.e. with a specific body region) can be accumulated to a total dose value for the respective body region.

Further, in step S700 a dose event planned for a specific body region of a specific patient could be analyzed with respect to its dose value compared to the accumulated dose value for that specific body region of that specific patient.

If a predetermined threshold, or reference value, for that specific body region is estimated to be exceeded by the planned dose event, step S700 may comprise issuing a dose alert, e.g. by an optic, acoustic and/or haptic signal.

In particular, the web interface accessed by the user via the user interface 30 may comprise a planning module for planning future dose events and may issue dose alerts in the described situation, e.g. by a pop-up windows, a sound alert and/or the like. In some advantageous embodiments, in step S700 an automated control signal may be issued for a medical imaging device, e.g. to automatically control the medical imaging device to lower a planned radiation intensity based and/or to display the dose reference value.

FIG. 3 shows a schematic block diagram illustrating a non-transitory computer-readable storage medium 200 according to the third embodiment of the present invention. The storage medium 200 comprises executable program code 250 configured to, when executed, perform the method according to the first embodiment of the present invention, preferably the method as described with respect to FIG. 2.

FIG. 4 shows a schematic block diagram illustrating a computer program product 300 according to the fourth embodiment of the present invention. The computer program product 300 comprises executable program code 350 configured to, when executed, perform the method according to the first embodiment of the present invention, preferably the method as described with respect to FIG. 2.

The embodiments have been chosen and described in order to best explain the principles of the invention and its practical applications, to thereby enable others skilled in the art to best utilize the invention and various embodiments with various modifications as are suited to the particular use contemplated.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for evaluating dose events of at least one medical imaging exam, comprising:
   determining whether a body region counter value is 1 or larger than 1, the body region counter value indicating a number of body regions;
   first associating all dose events of at least one list of dose events with a first standardized body region based protocol identifier among a set of standardized body region based protocol identifiers in response to determining the body region counter value is 1, the at least one list of dose events including the dose events of the at least one medical imaging exam;
   second associating each respective dose event of the at least one list of dose events with a corresponding second standardized body region based protocol identifier among the set of standardized body region based protocol identifiers in response to determining the body region counter value is larger than 1, the dose events among the at least one list of dose events being associated with a number of different second standardized body region based protocol identifiers among the set of standardized body region based protocol identifiers equal to the body region counter value;
   determining whether a combination of a planned radiation intensity and a total dose value for a first body region exceed a reference value, the first body region corresponding to the first standardized body region based protocol identifier or one of the second standardized body region based protocol identifiers, and the total dose value being based on an accumulation of dose values corresponding to dose events among the at least one list of dose events associated with the first body region; and
   automatically controlling a first medical imaging device to lower the planned radiation intensity for the first body region in response to determining the combination of the planned radiation intensity and the total dose value for the first body region exceed the reference value.

2. The method of claim 1, wherein the set of standardized body region based protocol identifiers includes identifiers for any or all of body regions including:
   abdomen, body, bone, breast, cervical spine, chest, extremities, extremity, face, head, lower extremity, lumbar spin, lumbosacral spine, neck, pelvis, skull, skull base to mid-thigh, spine, thoracic spine, thoracolumbar spine, upper extremity, and wholebody.

3. The method of claim 2, further comprising:
   providing the body region counter value including receiving a user input regarding a body region counter.

4. The method of claim 2, further comprising:
   providing the body region counter value including automatically determining the body region counter value based on the at least one list of dose events.

5. The method of claim 4, wherein the automatically determining of the body region counter value comprises:
   sequentially determining whether at least one criterion is met for each respective dose event among the at least one list of dose events; and
   increasing the body region counter value by 1 in response to determining the at least one criterion is met for the respective dose event.

6. The method of claim 5, wherein a first criterion of the at least one criterion is both whether the respective dose event is a topogram and whether another dose event among the at least one list of dose events is not a topogram, the other dose event being directly previous to the respective dose event with respect to the sequentially determining.

7. The method of claim 1, further comprising:
   providing the body region counter value including receiving a user input regarding a body region counter.

8. The method of claim 1, further comprising:
   providing the body region counter value including automatically determining the body region counter value based on the at least one list of dose events.

9. The method of claim 8, wherein the automatically determining of the body region counter value comprises:
   sequentially determining whether at least one criterion is met for each respective dose event among the at least one list of dose events; and
   increasing the body region counter value by 1 in response to determining the at least one criterion is met for the respective dose event.

10. The method of claim 9, wherein a first criterion of the at least one criterion is both whether the respective dose event is a topogram and whether another dose event among the at least one list of dose events is not a topogram, the other dose event being directly previous to the respective dose event with respect to the sequentially determining.

11. The method of claim 10, wherein a second criterion of the at least one criterion is whether a body phantom type set for the respective dose includes size different from that of a body phantom type set for the other dose event.

12. The method of claim 11, wherein a third criterion of the at least one criterion is whether a dose length product for the respective dose event is higher than a threshold value while a body part of the respective dose event is different from a body part of the other dose event.

13. The method of claim 12, wherein the threshold value is 130 mGy*cm.

14. The method of claim 6, wherein a second criterion of the at least one criterion is whether a body phantom type set for the respective dose event includes a size different from that of a body phantom type set for the other dose event.

15. The method of claim 14, wherein a third criterion of the at least one criterion is whether a dose length product for the respective dose event is higher than a threshold value while a body part of the respective dose event is different from a body part of the other dose event.

16. The method of claim 15, wherein the threshold value is 130 mGy*cm.

17. The method of claim 1, wherein the first associating and the second associating are based on at least one data field of property files of the dose events among the at least one list of dose events.

18. The method of claim 1, wherein
the at least one list of dose events includes a plurality of lists of dose; and
the method further comprises
checking whether at least two of the plurality of lists of dose events relate to a same real-world medical imaging exam, and
modifying the plurality of lists of dose events such that no real-word dose event is contained more than once among the plurality of lists of dose events in response to the checking.

19. The method of claim 18, wherein the checking includes comparing between the at least two of the plurality of lists at least one of:
a modality used to perform dose events;
a manufacturer of a second medical imaging device used to perform dose events;
a medical imaging device ID;
a patient ID of a patient;
a study date;
a medical imaging device type;
a tenant ID of a tenant;
a total dose value; or
a total scan duration.

20. A non-transitory computer-readable storage medium storing executable program code configured to, when executed by at least one processor, perform the method of claim 1.

21. A system for evaluating dose events of at least one medical imaging exam, comprising:
at least one processor configured to
determine whether a body region counter value is 1 or larger than 1, the body region counter value indicating a number of body regions,
first associate all dose events of at least one list of dose events, with a first standardized body region based protocol identifier among a set of standardized body region based protocol identifiers in response to determining the body region counter value is 1, the at least one list of dose events including the dose events of the at least one medical imaging exam,
second associate each respective dose event of the at least one list of dose events with a corresponding second standardized body region based protocol identifier among the set of standardized body region based protocol identifiers in response to determining the body region counter value is larger than 1, the dose events among the at least one list of dose events being associated with a number of different second standardized body region based protocol identifiers among the set of standardized body region based protocol identifiers equal to the body region counter value,
determine whether a combination of a planned radiation intensity and a total dose value for a first body region exceed a reference value, the first body region corresponding to the first standardized body region based protocol identifier or one of the second standardized body region based protocol identifiers, and the total dose value being based on an accumulation of dose values corresponding to dose events among the at least one list of dose events associated with the first body region, and
automatically controlling a first medical imaging device to lower the planned radiation intensity for the first body region in response to determining the combination of the planned radiation intensity and the total dose value for the first body region exceed the reference value.

22. The system of claim 21, wherein
the at least one list of dose events includes a plurality of lists of dose events; and
the at least one processor is configured to
check whether at least two of the plurality of lists of dose events relate to a same real-world medical imaging exam to obtain a check result, and
modify the plurality of lists of dose events such that no real-word dose event is contained more than once among the plurality of lists of dose events based on the check result.

23. The system of claim 22, wherein the at least one processor is configured to check whether the at least two of the plurality of lists of dose events received relate to the same real-world medical imaging exam including comparing between the at least two of the plurality of lists at least one of:
a modality used to perform dose events;
a manufacturer of a second medical imaging device used to perform dose events;
a medical imaging device ID;
a patient ID of a patient;
a study date;
a medical imaging device type;
a tenant ID of a tenant;
a total dose value; or
a total scan duration.

* * * * *

UNITED STATES PATENT AND TRADEMARK OFFICE
CERTIFICATE OF CORRECTION

| | |
|---|---|
| PATENT NO. | : 11,568,969 B2 |
| APPLICATION NO. | : 16/554997 |
| DATED | : January 31, 2023 |
| INVENTOR(S) | : Karlheinz Dorn |

It is certified that error appears in the above-identified patent and that said Letters Patent is hereby corrected as shown below:

On the Title Page

In the Foreign Application Priority Data (item (30)), the European patent application number that reads "8192023" should read --18192023--.

Signed and Sealed this
Tenth Day of September, 2024

Katherine Kelly Vidal
*Director of the United States Patent and Trademark Office*